United States Patent [19]

Schlapfer et al.

[11] Patent Number: 5,263,954

[45] Date of Patent: Nov. 23, 1993

[54] PEDICLE HOOK

[75] Inventors: Johannes F. Schlapfer, Glarus; Max Aebi, Bern, both of Switzerland

[73] Assignee: Synthes (U.S.A.), Paoli, Pa.

[21] Appl. No.: 893,922

[22] Filed: Jun. 4, 1992

[30] Foreign Application Priority Data

Jun. 5, 1991 [CH] Switzerland ............... 01676/91

[51] Int. Cl.⁵ ............................................. A61F 5/00
[52] U.S. Cl. ............................................. 606/61; 606/1;
606/53; 606/60
[58] Field of Search ............... 606/1, 53, 60, 61, 62,
606/72, 105; 623/17

[56] References Cited

U.S. PATENT DOCUMENTS

| 4,641,636 | 2/1987 | Cotrel | 606/61 |
| 5,074,864 | 12/1991 | Cozad et al. | |
| 5,084,049 | 1/1992 | Asher et al. | 606/60 |
| 5,112,332 | 5/1992 | Cozad et al. | |
| 5,116,334 | 5/1992 | Cozad et al. | |

FOREIGN PATENT DOCUMENTS

| 2044412 | 6/1991 | Canada. | |
| 0446092 | 9/1991 | European Pat. Off. | 606/61 |
| 9006646 | 6/1990 | Fed. Rep. of Germany. | |
| 2627690 | 2/1988 | France. | |
| 2640493 | 12/1989 | France. | |

OTHER PUBLICATIONS

Dubousset et al, Orthopaede, Nov. 89, Germany.

*Primary Examiner*—Stephen C. Pellegrino
*Assistant Examiner*—Glenn Dawson
*Attorney, Agent, or Firm*—Davis Hoxie Faithfull & Hapgood

[57] ABSTRACT

A pedicle hook for use in treatment of the spine has a bifurcated blade in which one of the legs formed by the bifurcation is longer than the other.

9 Claims, 4 Drawing Sheets

PEDICLE HOOK

FIELD OF THE INVENTION

This invention relates to a pedicle hook for use in the treatment of the spine, and in particular to a pedicle hook having a bifurcated blade.

BACKGROUND OF THE INVENTION

Pedicle hooks having bifurcated blades are described for example, in J. Dubousset and Y. Cotrel Orthopäde (1989) 18:118–127, "Die CD-Instrumentation in der Behandlung von Wirbel-Säulendeformitäten" (CD Instruments in the treatment of spinal column deformities). Such devices have a symmetrical indentation in the blade and can be used indiscriminately for the left and the right pedicles of the vertebral column. The purpose of the indentation in such hooks is to prevent the hook from sliding when a load is placed on it from the side, which can cause injury to the dura. Accordingly, an anatomically correct indentation that is as deep as possible is sought. The indentation of the blade of such prior pedicle hooks is centrally positioned and is completely symmetrical. Its medial and lateral dimensions are therefore equal. The height of the two legs formed by the bifurcation is limited by the width of the pedicle hook and the shape of the indentation, which in turn are adapted to the anatomy in question. In such symmetrical designs, the disadvantage is the continuing danger that the pedicle hook will slip medially under pressure and thereby injure the spinal marrow.

SUMMARY OF THE INVENTION

In accordance with the invention, a pedicle hook is provided having a bifurcated blade in which one of the legs formed by the bifurcation is larger than the other. Thus, the invention provides separate asymmetric hooks for placement on the left and right sides of the spinal column, leading to increased security of the implantation.

Specifically, the invention comprises a pedicle hook for the treatment of spinal column deformities comprising a shaft portion for attachment to a support bar and a curved bifurcated bladed hook attached to said shaft position, said blade being divided by said bifurcation into a lateral leg and a medial leg separated by an indentation, said lateral leg being longer than said medial leg.

The indentation in a hook according to the invention, is preferably asymmetrical which permits an increase in the lateral boundary of the indentation. This considerably reduces the danger that under pressure the pedicle hook will slide medially and injure the spinal marrow. On the other side, the medial boundary is less great, but this effect has no negative consequences so long as left and right pedicle hooks are assembled and longitudinal support bars connected with the pedicle hooks are assembled with the help of cross-rods, into a closed frame.

Another advantage of the invention is that thanks to the extended lateral boundary, the pedicle hook is guided laterally during operations at a very early stage, which facilitates assembly and makes it more secure.

The pedicle hook according to the invention can be attached to a longitudinal bar in a spinal column setting device in various known ways. For this purpose, the shaft portion of the pedicle hook according to the invention has appropriate structural components that permit its connection to a longitudinal support bar as described, for example, in EP-A 0 348 272.

The use of the pedicle hook according to the invention in clinical applications is completely analogous to that of known systems, and is described in detail in the publication by J. Dubousset and Y. Cotrel referred to above.

BRIEF DESCRIPTION OF THE DRAWINGS

The invention will be further described in connection with the appended drawings in which.

DETAILED DESCRIPTION OF THE INVENTION

Figure 1:
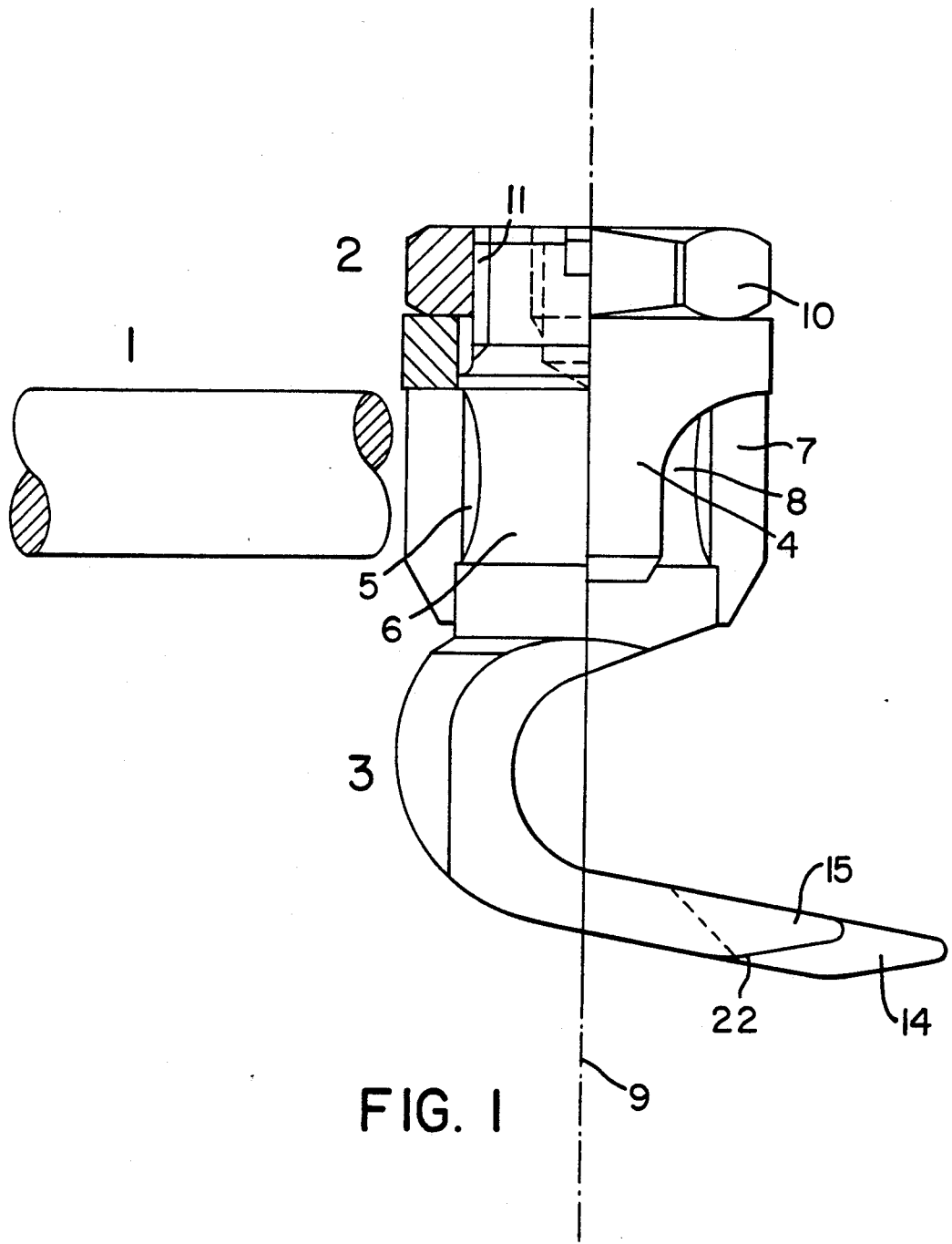
FIG. 1 is a view in side elevation and partly in vertical section of a pedicle hook according to the invention.

Referring to FIG. 1, a pedicle hook according to the invention comprises a shaft portion 2 that can be attached to a longitudinal support bar 1, and a curved blade 3, the end of which is bifurcated and connected to the shaft portion 2. The two legs 14 and 15 of the bifurcated blade are of different lengths. For the left pedicle 21 of the spinal column, as illustrated in FIG. 1, the lateral leg 14 is larger, e.g. 3.5 mm longer, than the medial leg 15. For the spinal column right pedicle 20, positioned to the right of the column marrow 18, the situation is exactly the reverse.

An indentation 22 is formed between legs 14 and 15. It is essentially a V, with a lateral inner edge 27 and a medial inner edge 28. The two inner edges 27 and 28 enclose angles 25, 26 (FIG. 5) of about 10° to the longitudinal central plate 23 of the hook. At its base 24 the indentation 22 is rounded.

Figure 2:
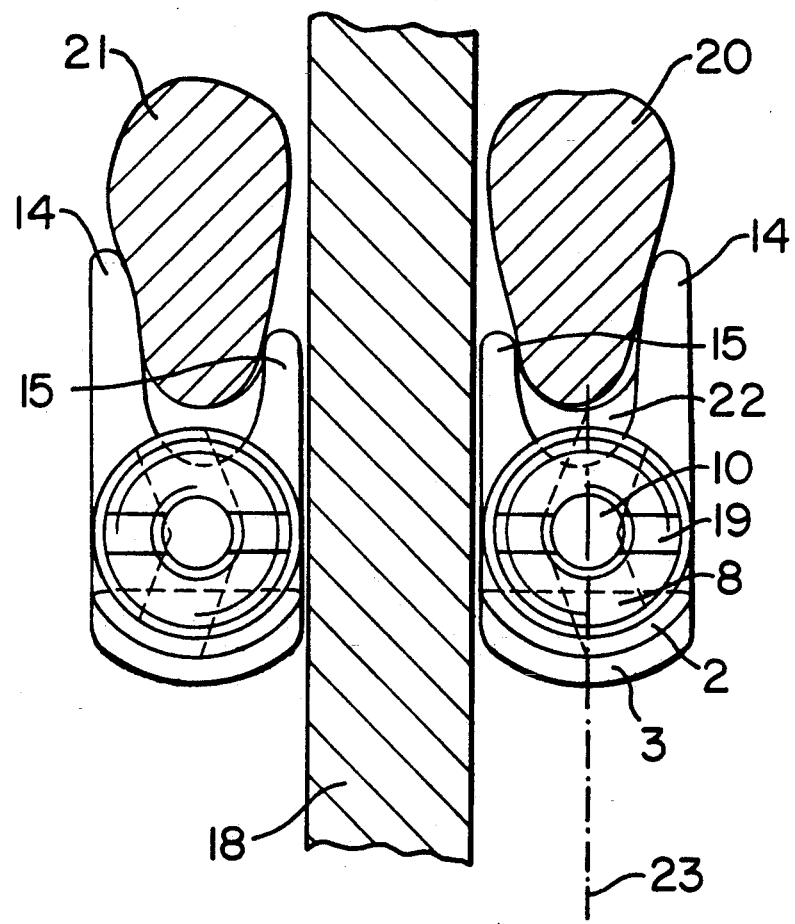
FIG. 2 is a schematic top view of pedicle hooks according to FIG. 1, mounted to the left and to the right of a spinal column.

In the preferred embodiment of the invention according to FIG. 2, the indentation 22, lying between the two legs 14 and 15, vis-à-vis the longitudinal central plane 23 of the pedicle hook, is shifted slightly medially, for example, by between about 0.1 mm and about 0.3 mm, and more preferably by 0.2 mm. The lateral leg 14 and the medial leg 15 may differ in length within the range of between about 2.0 mm and about 5.0 mm, and more specifically between about 3.0 mm and about 4.0 mm.

Figure 5:
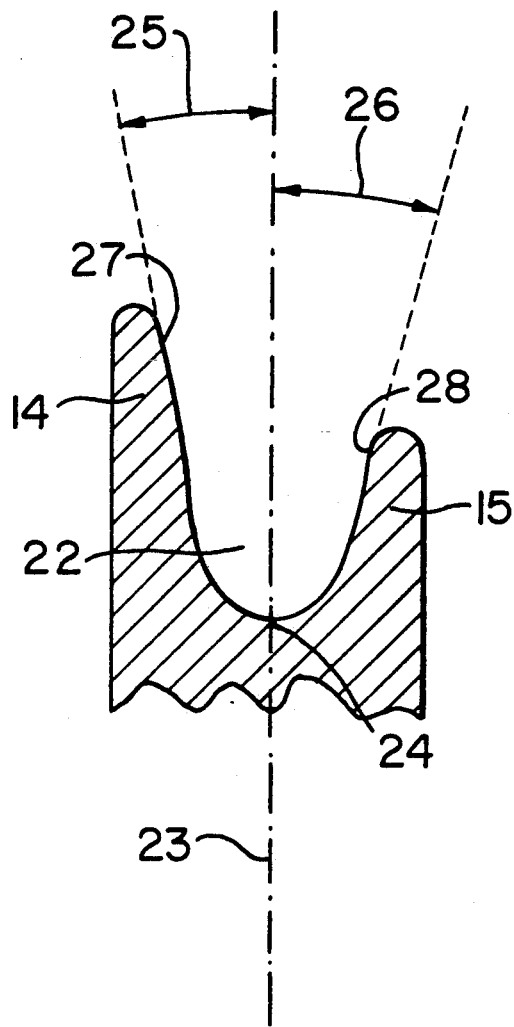
FIG. 5 is a partial cross-section in the area of the indentation of a pedicle hook according to the invention for mounting to the left of a spinal column.

However, the unequal legs 14 and 15 can also, as illustrated in FIG. 5, be maintained, through the selection of varying angles 25 and 26, between the lateral 27 and medial 28 inner edges of the legs and the longitudinal central plane 23 of the pedicle hook (medial larger than lateral) or through a combination of unequal angles 25 and 26 and offset position of the indentation 22. The difference between the two angles ranges between about 1° and about 2°. Therefore, the included angle between the two legs 14,15 is between about 18° and 22°.

In the embodiment illustrated in FIG. 1 and 2, the shaft portion 2 consists of the connector device described in the related Swiss Patent Application No.

1124/91 of the same applicants. It consists essentially of an external element 4 having a cylindrical hole 5 and an internal cylindrical element 6 that can slide coaxially in hole 5 and can rotate around its axis 9. Elements 4 and 6 have two common through openings 7 and 8, generally transverse to the axis 9 of the two elements 4 and 6, to receive the longitudinal bar 1. When the longitudinal bar 1 is introduced into the two holes 7 and 8, the axial sliding capability of internal element 6 in hole 5 of external element 4 is blocked in one direction, and its rotation is restricted to the angle area of through openings 7 and 8 of the two elements 4 and 6. Because of its through opening 8, internal element 6 can be flexibly distorted as against its axis 9. Moreover, it has an external thread 11 for engagement with a nut 10. Tightening nut 10 causes an axial deformation of internal element 6 which causes an axial sliding of internal element 6 relative to external element 4. The flexibly deformable internal element 6 expands, and there is a deformation of the internal element 6 within hole 5 of external element 4 with simultaneous locking of the connector device as a whole and the longitudinal bar 1 inserted into it. The nut 10 may be tightened or loosened by means of a wrench and an instrument suitable for holding the pedicle hook in position when the nut 10 is manipulated. The wrench may be inserted like a screwdriver into the longitudinal slot 19 (FIG. 2) of the nut 10.

Instead of the above-described preferred connector device for the shaft section 2, any other known connection systems can also be used to attach the shaft portion 2 to a longitudinal bar 1, for example the structure shown in EP-A1 348 272.

Figure 4:
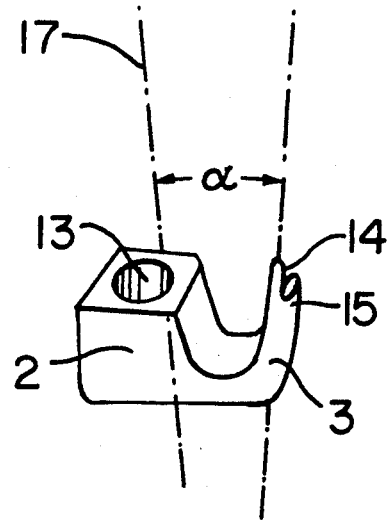
FIG. 4 is a perspective view of a pedicle hook according to the invention for mounting on the right side of a spinal column.
Figure 3:
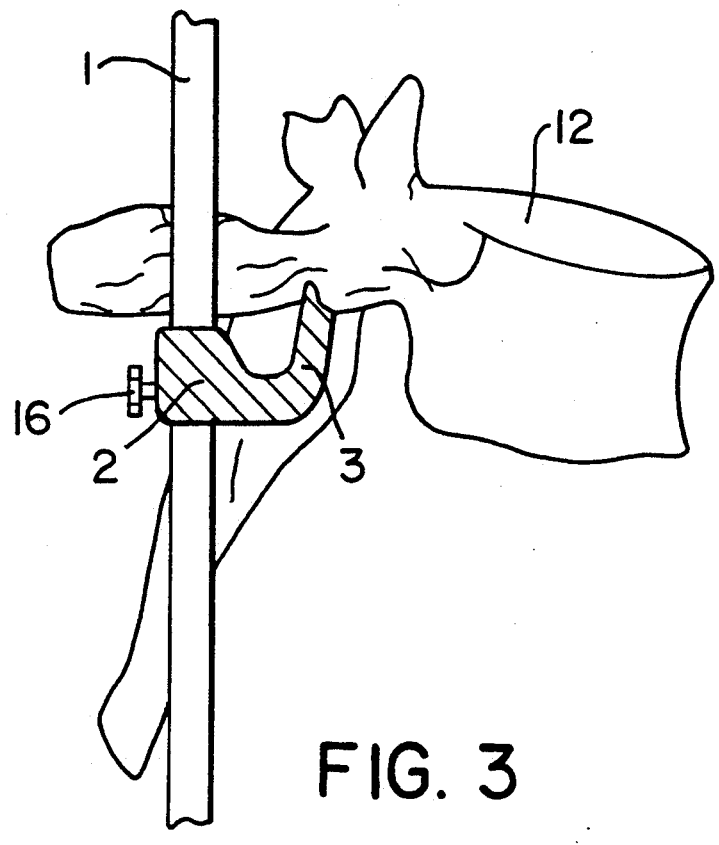
FIG. 3 is a schematic side view of a pedicle hook according to the invention, mounted to the right of a spinal column.

FIG. 3 shows the insertion of the pedicle hook at the rear transition of the right pedicle into the lamina of a vertebral body 12. In the embodiment according to FIG. 3, the shaft 2, as illustrated in FIG. 4 in detail, has a channel 13 to hold the longitudinal bar 1, which can be fixed by means of screw 16. The two legs 14 and 15 of hook blade 3 of the pedicle hook are bent ventrally toward the longitudinal axis 17 defined by the longitudinal bar 1 at an angle α of about 10°.

What is claimed is:

1. Pedicle hook for the treatment of spinal column deformities, comprising a shaft portion for attachment to a support bar, said shaft portion having a longitudinal central plane and a central axis in said longitudinal central plane, and a curved bifurcated blade attached to said shaft portion, said blade having two sides and being divided by said bifurcation into a lateral leg and a medial leg, said lateral leg being longer than said medial leg, said lateral leg and said medial leg forming an indentation between them, and said longitudinal central plane being equidistant from the two sides of said blade.

2. Pedicle hook according to claim 1, wherein the indentation is V-shaped, enclosing an angle between said two legs of about 18° and about 22°.

3. Pedicle hook according to claim 2, characterized by the fact that an inner edge of the lateral leg encloses a smaller angle to the longitudinal central plane of the pedicle hook than an inner edge of its medial legs.

4. Pedicle hook according to claim 3, wherein the difference between the two angles is between about 1° and about 2°.

5. Pedicle hook according to claim 1, wherein the indentation has a rounded bottom.

6. Pedicle hook according to claim 1, wherein the difference in length between the lateral and the medial legs ranges between about 2.0 and about 5.0 mm.

7. Pedicle hook according to claim 6, wherein the difference in length is between about 3.0 and about 4.0 mm.

8. Pedicle hook according to claim 1, wherein the indentation between the lateral and medial legs is displaced medially with respect to the longitudinal central plane of the hook.

9. Pedicle hook according to claim 8, wherein the indentation is displaced between about 0.1 and about 0.3 mm.

* * * * *